United States Patent [19]
Tanaka et al.

[11] Patent Number: 6,060,109
[45] Date of Patent: *May 9, 2000

[54] ATOMIC ABSORPTION ANALYSIS FOR MEASURING AND CONTROLLING THE AMOUNT OF A METAL VAPOR IN VAPOR DEPOSITION COATING LINE AND APPARATUS THEREFOR

[75] Inventors: Hiroshi Tanaka; Yasushi Fukui; Minoru Saito, all of Sakai, Japan

[73] Assignee: Nisshin Steel Co., Ltd., Japan

[*] Notice: This patent issued on a continued prosecution application filed under 37 CFR 1.53(d), and is subject to the twenty year patent term provisions of 35 U.S.C. 154(a)(2).

[21] Appl. No.: 08/822,433

[22] Filed: Mar. 21, 1997

[30] Foreign Application Priority Data

| Mar. 27, 1996 | [JP] | Japan | 8-099314 |
| Jan. 22, 1997 | [JP] | Japan | 9-009487 |
| Jan. 22, 1997 | [JP] | Japan | 9-009488 |
| Feb. 13, 1997 | [JP] | Japan | 9-028762 |

[51] Int. Cl.[7] ................................................. C23C 14/54
[52] U.S. Cl. ........................... 427/8; 427/250; 427/251
[58] Field of Search ............................. 427/8, 250, 251; 118/690, 715, 729

[56] References Cited

U.S. PATENT DOCUMENTS

| 4,587,134 | 5/1986 | Shimozato et al. | 427/251 |
| 5,776,254 | 7/1998 | Yuuki et al. | 118/725 |

FOREIGN PATENT DOCUMENTS

| 59-147239 | 8/1984 | Japan . |
| 59-147240 | 8/1984 | Japan . |
| 60-133308 | 7/1985 | Japan . |

OTHER PUBLICATIONS

Ustimenko et al., Zh. Anal. Khim., 44(1), pp. 177–178 (No Month), 1989.

English–language Abstract of Japanese Patent Application Laid–Open No. 60–133308, entitled "Method for Measuring Attached Amount of Plated Film", Jul. 16, 1985, 1 p.

*Primary Examiner*—Timothy Meeks
*Attorney, Agent, or Firm*—Webb Ziesenheim Logsdon Orkin & Hanson, P.C.

[57] ABSTRACT

A metal vapor 12 passing through a guide duct 13 from a vapor source 10 to a steel strip 1 is sampled through a takeoff pipe 14 to a measuring chamber 15. The metal vapor is irradiated with a measuring beam 20 in the chamber 15, to detect the absorbance of luminous energy in the metal vapor. The detected value of absorbance is used for the quantitative calculation of the metal vapor 12 passing through the guide duct 13, and the opening ratio of a shutter 17 provided in the guide duct 13 is adjusted on the basis of the calculation result so as to control the flow amount of the metal vapor 12 passing through the guide duct 13. In the case where a large amount of the metal vapor 12 passes through the guide duct 13, the amount of the metal vapor 12 reaching the measuring beam 20 is reduced by partially discharging the metal vapor 12 from the measuring chamber 15. Since the deposition amount of a plating metal is directly controlled in response to the amount of the metal vapor 2 passing through the guide duct 13, the amount of a deposited plating layer is controlled with high accuracy and with a quick response time in a continuous vapor deposition coating line.

2 Claims, 11 Drawing Sheets flow rate (g/m² · sec.) of Zn vapor passing through the guide duct

6,060,109

ATOMIC ABSORPTION ANALYSIS FOR MEASURING AND CONTROLLING THE AMOUNT OF A METAL VAPOR IN VAPOR DEPOSITION COATING LINE AND APPARATUS THEREFOR

BACKGROUND OF THE INVENTION

The present invention relates to a method and apparatus for rapidly controlling the amount of a plating metal deposited in the vapor deposition process for manufacturing a coated steel strip and also relates to an atomic absorption analysis for measuring the amount of a metal vapor carried from a vapor source to a steel strip with high accuracy and high reliability.

In a vapor deposition process line for manufacturing a Zn—coated steel sheet or the like, it is known to measure the amount of a deposited plating metal by fluorescent X-ray spectroscopy or X-ray diffraction techniques.

The use of fluorescent X-ray spectroscopy for this purpose is disclosed in Japanese Patent Application Laid-Open 60-13308. The intensity of fluorescent X-rays emitted from a plating metal by the irradiation of the coated steel sheet with X-rays is measured and compared with a predetermined analytical curve. The amount of deposited plating metal is then calculated from the detected value of the intensity.

According to the fluorescent X-ray spectroscopy technique, an X-ray measuring device 9 shown in FIG. 1 is located at an outlet side of a vapor deposition coating line. A steel strip 1 is carried through a gas reducing furnace 2 wherein the surface of the steel strip 1 is activated. The steel strip is then introduced through inlet hermetic rollers 3 into a vacuum chamber 4. In the vacuum chamber 4, Zn and Mg are vapor deposited to the steel strip 1 in a vapor deposition zone 5. The steel strip 1 is then carried from the vacuum chamber 4 through outlet hermetic rollers 6 and a cooling zone 7.

The X-ray measuring device 9 is located at a position facing the surface of the vapor deposition coated steel strip 8 exiting the vacuum chamber 4. The physical location of the measuring device 9 causes a long time lag in measuring the amount of the deposited plating metal after the vapor deposition. Consequently, operational conditions cannot be quickly controlled in response to changes in the measured deposition amount.

On the other hand, the X-ray diffraction method is suitable for analysis of a coated steel sheet having a multi-layered plating layer. In this method, the peak intensity peculiar to the plating composition is measured, and the deposition amount is calculated by solving the equation relating to the plating composition and the deposition amount.

When different kinds of metals are vapor deposited so as to form a multi-layered plating layer such as a Zn—Mg vapor deposition layer, it is necessary to measure and control the deposition amount of each metal. However, it is difficult to detect the deposition amount of each metal with high accuracy, since X-rays emitted from each sublayer are decayed by the other metal and the other sublayer. In the case of a Zn—Mg plating layer having a multi-layered structure, X-rays emitted from Mg are especially weak and easily decayed by Zn and the alloyed sublayers, making the accurate measurement of the deposition amount fairly difficult.

In addition, in the X-ray diffraction method, the point of measurement is spaced apart from the vapor deposition zone. This space layout location creates long time delays to obtain a measuring result and thus prevents accurate control of the deposition amount.

In the case of a plating layer having a multi-layered structure composed of different kinds of metals including several kinds of intermetallic compounds, it is necessary to measure the peak intensity of each intermetallic compound, using many measuring devices. In addition, since each peak intensity is decayed by the other metal, alloys and sublayers cause measurement errors. Hence, the deposition amount cannot be measured with high reliability in these multi-layered structure.

In addition, the vapor deposition of Zn or Mg onto an inner surface of an apparatus is inhibited by holding said surface at a temperature of several hundreds of degree C, and Zn or Mg vapor is carried from a vapor source through a guide duct to a steel strip. If the amount of a metal vapor passing though the guide duct can be directly measured, the deposition amount of a plating metal is directly controlled with high accuracy.

SUMMARY OF THE INVENTION

The inventors observed that atomic absorption analysis may be used for measuring the amount of a metal vapor passing through a guide duct. In atomic absorption analysis, a metal vapor is irradiated with a beam of absorbable wavelength, and the amount of the metal vapor is detected as the value of absorption in the metal vapor.

The inventors have discovered that the detected value of absorption accurately represents the amount of the metal vapor passing through the guide duct and that the detected value of absorption instantaneously changes in proportion to the amount of the metal vapor passing through the guide duct. In this regard, atomic absorption analysis has various advantages for measuring the amount of the metal vapor and controlling the amount of the metal vapor deposited on a steel strip.

The first object of the present invention is to enable the on-line control of the deposition amount with quick response based on the amount of a metal vapor passing though a guide duct measured by an atomic absorption photometer.

The second object of the present invention is to detect the degree of absorbance with high sensitivity to the change of the amount of a metal vapor passing through a guide duct.

The third object of the present invention is to enable the measurement of absorbance without saturation, even when a high concentration of large amount of a metal vapor is carried through a guide duct.

According to the present invention, a metal vapor carried from a vapor source through a guide duct to a steel strip is sampled through a takeoff pipe to a measuring chamber. The takeoff pipe has one end opened to the guide duct and the other end opened to the measuring chamber. An inlet pipe of small aperture may be attached to the takeoff pipe at the end opened to the measuring chamber.

An atomic absorption photometer is provided in the measuring chamber. The photometer comprises a light source for emitting a measuring beam of specified wavelength absorbable in a metal vapor and a detector for receiving the measuring beam after the irradiation of the metal vapor. When the metal vapor is irradiated with the measuring beam, the luminous energy of the beam is absorbed in the metal vapor. The degree of absorbance is detected by the detector located at a position opposite to the light source.

The amount of the metal vapor passing through the guide duct is calculated from the detected value of absorbance, and the calculation result is outputted as a command for adjusting an opening ratio of a controlling shutter provided in the guide duct.

In the case where the inflow of the metal vapor reaching the measuring beam is too great, the absorbance is saturated but absorbance does not increase any more in spite of the increase of the amount of the metal vapor. In such case, the amount of the metal vapor reaching the measuring beam is reduced by partially discharging the metal vapor from the measuring chamber or by partially depositing the metal vapor on the inner wall of the measuring chamber before irradiation of the balance of the metal vapor with the measuring beam.

The reduction in the amount of metal vapor reaching the measuring beam is achieved by dividing the measuring chamber into a plurality of compartments. That is, the measuring chamber is divided into a front compartment(s) and a rear compartment by the partition wall(s) in which an opening is formed to permit communication between the front compartment(s) with the rear compartment, each compartment being individually evacuated by a separately provided vacuum pump. The opening allows the partial flow of the metal vapor from the front compartment to the next compartment or the rear compartment where an atomic absorption photometer is provided.

The metal vapor sampled from the guide duct is carried through the takeoff pipe to the front compartment and then partially carried to the rear compartment through the opening(s). The metal vapor is reduced in the front compartment in an amount sufficiently smaller than the amount needed to saturate the absorbance, and then the reduced amount of metal vapor flows to the rear compartment. The metal vapor carried to the rear compartment is then irradiated with the measuring beam in the same manner described above.

The degree of reduction in the amount of the metal vapor reaching the measuring beam is controlled by adjusting the number of the partition walls, the aperture of the opening(s) for the passage of the metal vapor, and the position to form the opening(s) in the partition wall(s). When the opening for the passage of the metal vapor is formed in the partition wall at a position deviated from an extension line of the takeoff pipe, the amount of metal vapor reaching the measuring beam is effectively reduced. To the same effect, the opening for the passage of the metal vapor may be formed in one partition wall at a position deviated or offset from another opening formed in the adjacent partition wall.

The metal vapor reaching the measuring beam may be reduced in amount by discharging most of the metal vapor together with nitrogen gas through an exhaust pipe connected to a vacuum pump. The nitrogen gas is preferably introduced through a supply pipe provided at one side wall to the measuring chamber along a direction vertical to the inflow of the metal vapor and discharged through the exhaust pipe provided at the opposite side wall so as to efficiently discharge the metal vapor together with the nitrogen gas. In the case where the measuring chamber has a plurality of supply pipes and a plurality of exhaust pipes, the metal vapor carried into the measuring chamber is remarkably reduced step by step to a value at which the absorbance of luminous energy is not saturated.

DETAILED DESCRIPTION OF THE PREFERRED EMBODIMENTS

Figure 1:
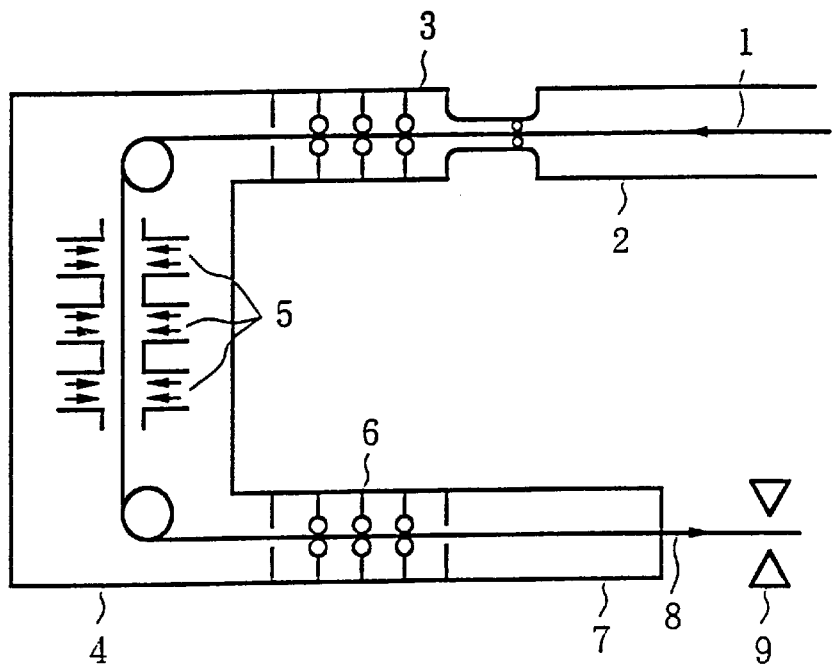
FIG. 1 is a schematic view of a conventional fluorescent X-ray method for measuring the amount of a deposited plating metal.
Figure 2:
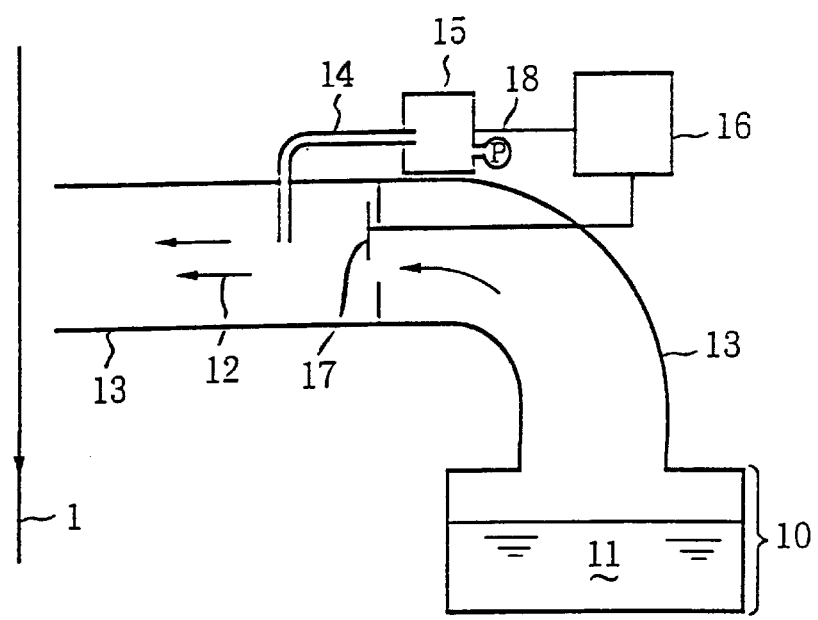
FIG. 2 is a schematic view illustrating a guide duct through which a metal vapor is carried from a vapor source to a steel strip for vapor deposition coating.

According to the present invention, as shown in FIG. 2, the amount of a metal vapor is measured by atomic absorption analysis, using a takeoff pipe 14 having one end opened to a guide duct 13 and the other end opened to a measuring chamber 15.

A metal 11 in a vapor source 10 is evaporated and carried as a metal vapor 12 through the guide duct 13 to a steel strip 1 to be vapor deposition coated. The metal vapor 12 passing through the guide duct 13 is sampled through the takeoff pipe 14.

The sampled metal vapor 12 is carried through the takeoff pipe 14 to the measuring chamber 15 which is evacuated by a vacuum pump 18. The amount of the sampled metal vapor 12 is proportional to the difference between the internal pressures of the guide duct 13 and the measuring chamber 15.

Figure 3:
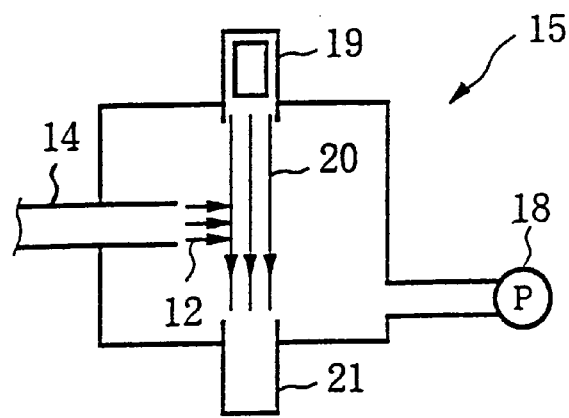
FIG. 3 is a schematic view illustrating a measuring chamber wherein a metal vapor is irradiated with a measuring beam.

As shown in FIG. 3, a hollow cathode lamp which emits a measuring beam 20 of specified wavelength absorbable in the metal vapor 12 is provided as a light source 19 in the measuring chamber 15. A photomultiplier is provided as a detector 21 at the position opposite to the light source 19 in the measuring chamber 15.

The sampled metal vapor 12 introduced into the measuring chamber 15 is irradiated with the measuring beam 20 to undergo atomic absorption and a portion of the beam which is not absorbed in the metal vapor 12 reaches the detector 21. When the luminous energy measured by the detector 21 is compared with that emitted from the light source 19, the luminous energy absorbed in the metal vapor 12, i.e. absorbance, is detected. The absorbance represents the amount of the sampled metal vapor which is in proportion to the amount of the metal vapor 12 passing through the guide duct 13.

The detected value of absorbance is transformed to an electrical signal and outputted to a computer 16, shown in FIG. 2. In the computer 16, the inputted value is compared with a preset analytical curve to calculate the amount of the metal vapor. Since the deviation of the vapor amount obtained by the atomic absorption method is in a positive relationship with the deviation of the metal vapor 12 passing through the guide duct 13, the amount of the metal vapor 12 passing through the guide duct 13 can be calculated from the measurement result on the amount of the sampled metal vapor.

The calculation result is outputted as a command for controlling the opening ratio of a shutter 17 provided in the guide duct 13. Consequently, the amount of the metal vapor 12 passing through the guide duct 13 is controlled to the preset value. The shutter 17 is preferably located at a position near the opening of the takeoff pipe 14 to improve the responsibility of control.

The absorbance is increased as the inflow amount of the sampled metal vapor 12 introduced through the takeoff pipe 14. However, when the metal vapor 12 in an amount more than a predetermined value is introduced, the absorbance is saturated and does not increase any more. The situation where the absorbance is not increased is variable in response to the kind of the metal vapor 12, the wavelength and intensity of the measuring beam 20, among other factors.

In this regard, in order to measure the amount of metal vapor with high accuracy even in the abovementioned case, it is necessary to reduce the sampled metal vapor 12 reaching measuring beam 20 in an amount sufficiently smaller than the value at which the absorbance is saturated.

The metal vapor could be reduced in amount by using a takeoff pipe 14 having a smaller inner diameter. However, the resistance of the takeoff pipe 14 against the inflow of the metal vapor 12 becomes stronger as the inner diameter of the takeoff pipe 14 becomes smaller. The resistance causes the delay in the change of the inflow amount of the metal vapor 12 passing through the takeoff pipe 14 to the measuring chamber 15 from the change of the flow amount of the metal vapor 12 carried through the guide duct 13.

The delay in response could be overcome by making the inner diameter of the takeoff pipe 14 smaller only at its top end. However, an industrially possible lower limit of the inner diameter is on the order of 0.1 mm, although a much smaller inner diameter is required for the takeoff pipe 14. In addition, such a takeoff pipe 14 having a very small inner diameter at its top end is easily deformed with heat. The deformation causes significant fluctuations in the amount of metal vapor 12 introduced into the measuring chamber 15 and causes measuring errors. That is, designing the takeoff pipe 14 has its limit to suppress the inflow amount of the sampled metal vapor 12.

In such case, the measuring chamber 15 is preferably divided into a plurality of compartments by a partition wall(s) to cause a reduction of the metal vapor 12 reaching the measuring beam 20.

Figure 4:
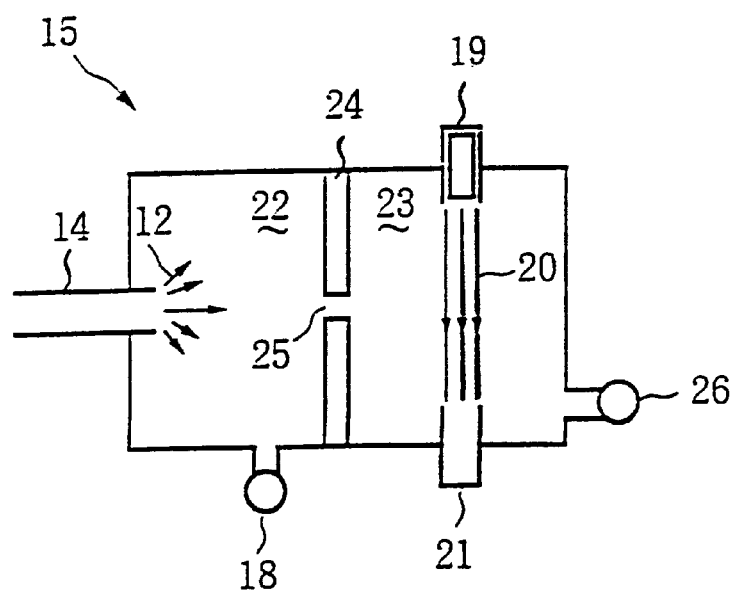
FIG. 4 is a schematic view illustrating a measuring chamber which is divided into front and rear compartments by one partition wall.

The measuring chamber 15 shown in FIG. 4 is divided into a front compartment 22 and a rear compartment 23 by a partition wall 24. An opening 25 is formed in the partition wall 24 to permit communication between the front compartment 22 and the rear compartment 23. The takeoff pipe 14 is opened to the front compartment 22 for the inflow of the sampled metal vapor 12. The front and rear compartments 22, 23 are individually evacuated by vacuum pumps 18, 26, respectively. An inlet pipe 27 (shown in FIG. 15) may be attached to the opening of the takeoff pipe 14 exposed to the interior of the front compartment 22, in order to reduce the inflow amount of the metal vapor 12.

Due to this construction, only a part of the metal vapor 12 diffused through the takeoff pipe 14 into the front compartment 22 flows through the opening 25 into the rear compartment 23, so as to limit the amount of the metal vapor 12 reaching the measuring beam 20. The metal vapor 12 which does not flow into the rear compartment 23 is deposited on the partition wall 24 or discharged to the outside by the vacuum pump 18. In the case where the deposition on the partition wall 24 is unfavourable, the partition wall 24 may be optionally heated. The deposition on the takeoff pipe 14 is inhibited in the same way, namely by holding the takeoff pipe at an elevated temperature.

The metal vapor 12 reaching the measuring beam 20 may be sufficiently reduced in amount by adjusting the aperture of the opening 25 and by the number of the partition walls 24 provided in the measuring chamber 15.

Figure 5:
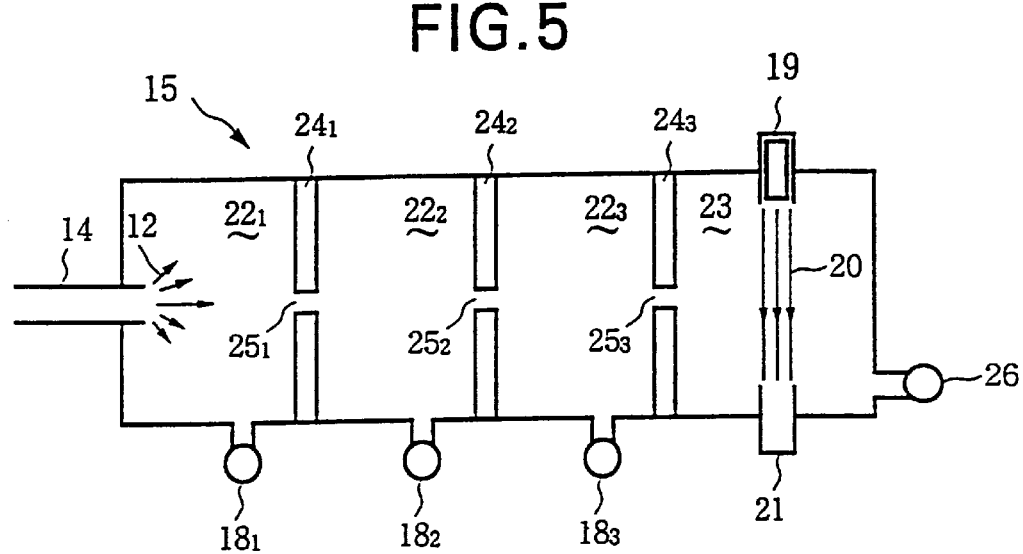
FIG. 5 is a schematic view illustrating a measuring chamber which is divided into a plurality of front compartments and a rear compartment.

For instance, the interior of the measuring chamber 15 may be divided into a plurality of front compartments $22_1$, $22_2$, $22_3$ and a rear compartment 23 by a plurality of partition walls $24_1$, $24_2$, $24_3$, as shown in FIG. 5. Each front compartment $22_1$, $22_2$, $22_3$ or the rear compartment 24 communicates with the adjacent compartment through an opening $25_1$, $25_2$, $25_3$. The compartments $22_1$, $22_2$, $22_3$ are individually evacuated by vacuum pumps $18_1$, $18_2$, $18_3$ separately provided at the compartments $22_1$, $22_2$, $22_3$. The number of the partition walls $24_1$, $24_2$, $24_3$ is properly determined in response to the amount of the metal vapor 12 reaching the measuring beam 20. Due to the presence of said partition walls $24_1$, $24_2$, $24_3$, the metal vapor 12 reaching the measuring beam 20 is sufficiently reduced in amount compared with the amount of the metal vapor 12 flowing from the takeoff pipe 14 to the front compartment $22_1$.

Figure 6:
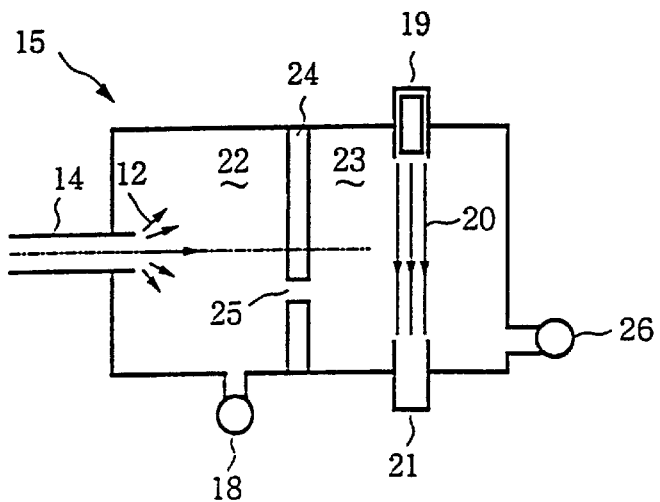
FIG. 6 is a schematic view illustrating a measuring chamber which is divided by a partition wall having an opening formed at a position offset from the longitudinal axis of a takeoff pipe.

The location of the opening 25 in the partition wall 24 at a position offset from the longitudinal axis of the takeoff pipe 14, as shown in FIG. 6, is also effective for reducing the amount of the metal vapor 12 reaching the measuring beam 20. The metal vapor 12 carried through the takeoff pipe 14 to the front compartment 22 is distributed such that the amount of metal vapor 12 is greatest along the longitudinal axis of the takeoff pipe 12 and less at a position further from the longitudinal axis. Therefore, the offset opening 25 shown in FIG. 6 effectively reduces the amount of the metal vapor 12 reaching the measuring beam 20.

The front compartment 22 shown in FIG. 6 is filled with the metal vapor 12 carried through the takeoff pipe 14. Only a part of said metal vapor 12 flows through the opening 25 into the rear compartment 23, while the balance of the metal vapor 12 is discharged by the vacuum pump 18 or deposited on the inner wall of the front compartment 22. The amount of metal vapor 12 filling the front compartment 22 is greatest along the longitudinal axis of the takeoff pipe 14 and smallest at a position laterally offset from the longitudinal axis. Consequently, in the case where the opening 25 is laterally offset from the longitudinal axis of the takeoff pipe 14, the amount of metal vapor 12 passing through the opening 25 becomes smaller as the offset distance of the opening 25 from the longitudinal axis of the takeoff pipe 14 becomes greater.

The metal vapor 12 having passed through the opening 25 fills the rear compartment 23, and is discharged by the vacuum pump 26 or is deposited on the inner wall of the rear compartment 23. A part of said metal vapor 12 reaches the measuring beam 20 prior to being discharged or deposited. The amount of the metal vapor 12 passing through the guide duct 13 is calculated based upon the amount of the metal vapor 12 reaching the measuring beam 20.

Figure 7:
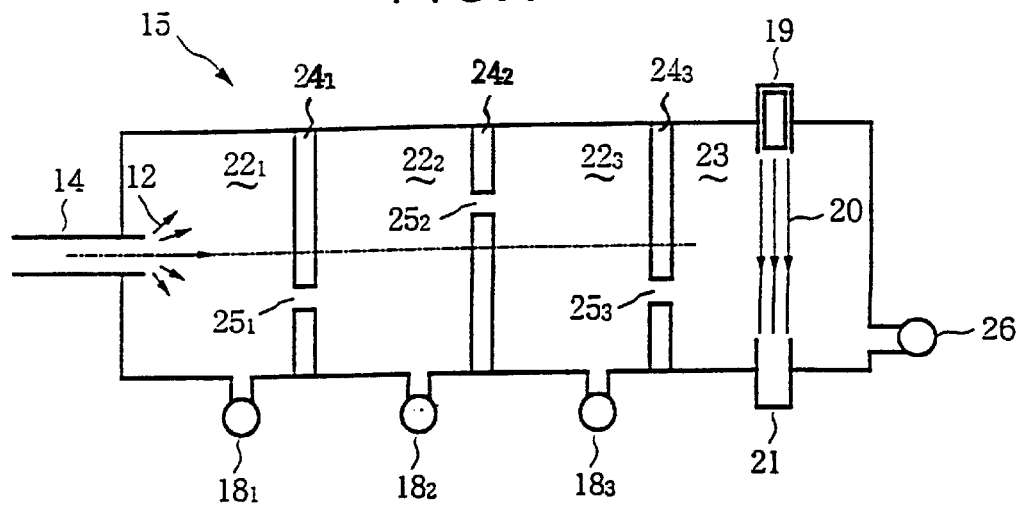
FIG. 7 is a schematic view illustrating a measuring chamber which is divided by a plurality of partition walls each having an opening formed at a position offset from the longitudinal axis of a takeoff pipe.

In the case where a plurality of partition walls $24_1$, $24_2$, $24_3$ is provided in the measuring chamber 15, the openings $25_1$, $25_2$, $25_3$ are advantageously formed in the partition walls $24_1$, $24_2$, $24_3$ at respective positions which are each offset from the other, as shown in FIG. 7, in order to more reduce the amount of metal vapor 12 reaching the measuring beam 20.

In any case, the amount of the metal vapor 12 passing through the guide duct 13 is in positive correlation with the amount of the metal vapor 12 passing through the openings 25, $25_1$, $25_2$, $25_3$ and the amount of the metal vapor 12 reaching the measuring beam 20. Therefore, the amount of the metal vapor 12 flowing through the takeoff pipe 14 to the measuring chamber 15, in other words, the amount of the metal vapor 12 passing through the guide duct 13, is detected by measuring the degree of absorbance in the metal vapor 12 reaching the measuring beam 20.

With reference to FIGS. 6 and 7, the metal vapor 12 carried through the takeoff pipe 14 to the front compartment 22, $22_1$ is deposited on the partition wall 24, $24_1$ or discharged by the vacuum pump 18, $18_1$, and only a part of said metal vapor 12 is introduced through the opening 25, $25_1$ to the rear compartment 23 or the next front compartment $22_2$. Consequently, the metal vapor 12 reaching the measuring beam 20 is sufficiently reduced in amount to a level at which atomic absorption analysis is enabled without the saturation of absorbance, as compared with the amount of metal vapor 12 carried through the takeoff pipe 14 to the front compartment 22, $22_1$. The amount of the metal vapor 12 reaching the measuring beam 20 instantaneously varies in response to the changed amount of the metal vapor 12 passing through the guide duct 13. The instantaneous change in amount assures the accurate measurement of the amount of the metal vapor 12 and with a quick response time.

Figure 8:
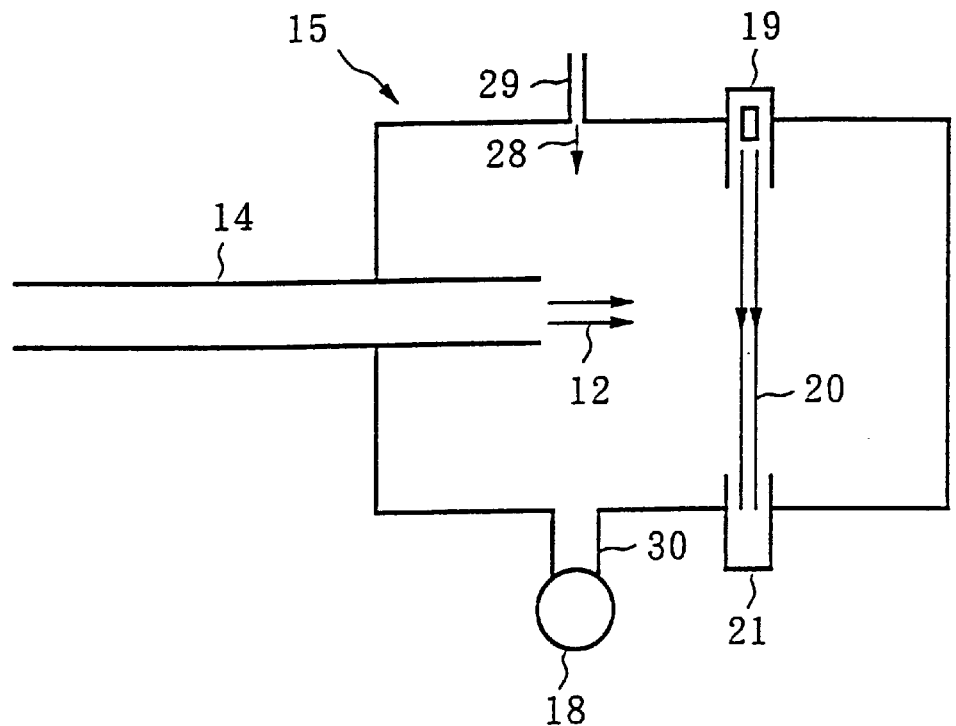
FIG. 8 is a schematic view of a measuring chamber which has a nitrogen gas supply pipe provided at one side wall and an exhaust pipe provided at the opposite side wall.

The metal vapor 12 reaching the measuring beam 20 also may be reduced in amount by supplying nitrogen gas 28 through a supply pipe 29 along a direction vertical to the flow axis of the metal vapor 12, as shown in FIG. 8. The nitrogen gas supply pipe 29 is opened to the measuring chamber 15 at one side wall, while an exhaust pipe 30 connected to a vacuum pump 18 is opened to the measuring chamber 15 at the opposite side wall.

Since the supply pipe 29 and the exhaust pipe 30 are provided at the measuring chamber 15 as mentioned above, most of the metal vapor 12 introduced through the takeoff pipe 14 is discharged together with the nitrogen gas 28 from the measuring chamber 15 through the exhaust pipe 30. Consequently, the metal vapor 12 reaching the measuring beam 20 is remarkably reduced in amount compared with the metal vapor 12 carried through the takeoff pipe 14 into the measuring chamber 15, so as to enable atomic absorption analysis at a low vapor pressure vapor which does not saturate absorbance.

Figure 9:
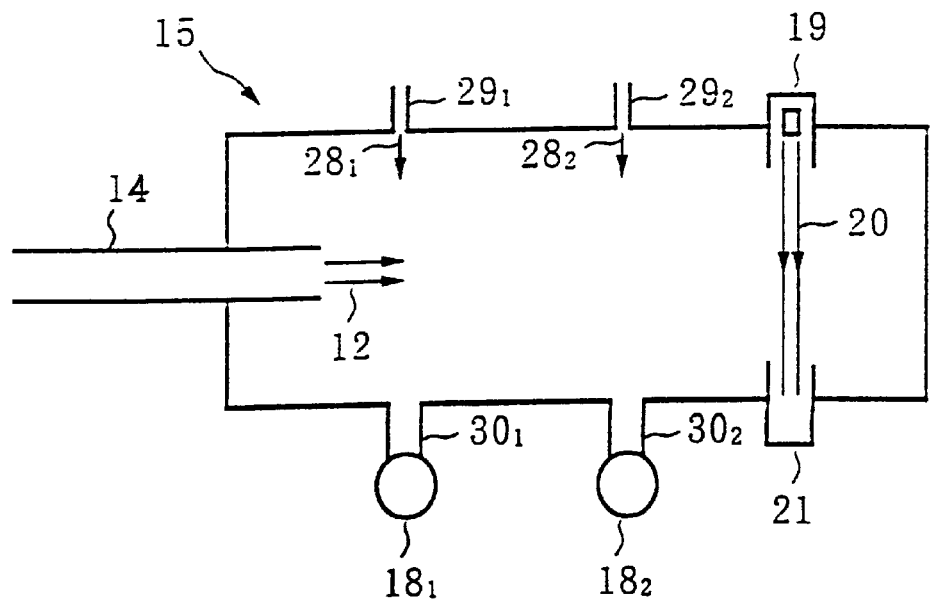
FIG. 9 is a schematic view of a measuring chamber which has a plurality of nitrogen gas supply pipes provided at one side wall and a plurality of exhaust pipes provided at the opposite side wall.

A plurality of nitrogen gas supply pipes $29_1$, $29_2$ and a plurality of exhaust pipes $30_1$, $30_2$ may be provided at the measuring chamber 15, as shown in FIG. 9. In this case, the metal vapor 12 carried through the takeoff pipe 14 into the measuring chamber 15 is discharged in two steps, i.e. the first discharging step with the nitrogen gas $28_1$ is supplied through the pipe $29_1$ and the second discharging step with the nitrogen $28_2$ is supplied through the pipe $29_2$. Therefore, the amount of metal vapor 12 reaching the measuring beam 20 is greatly reduced, so that the atomic absorption analysis is performed with high accuracy.

FIGS. 8 and 9 show the exhaust pipes 30, $30_1$, $30_2$ opened to the measuring chamber 15 at a position on one side wall which is symmetric to the position on the opposite side wall where the inlets of the nitrogen gas supply pipes 29, $29_1$, $29_2$ are located with respect to the longitudinal axis of the takeoff pipe 14. However, said symmetric arrangement is merely one example, but not restrictive of the scope of the present invention. As long as the nitrogen gas 28, $28_1$, $28_2$ supplied through each of the pipes 29, $29_1$, $29_2$ is efficiently discharged, the position of each of the exhaust pipes 30, $30_1$, $30_2$ may be freely determined.

In this case, an inlet pipe 27 (shown in FIG. 18) may be attached to the end of the takeoff pipe 14 also opened to the measuring chamber 15. The inlet pipe 27 has a small aperture therein for the passage of the metal vapor 12. The inlet pipe 27, in effect, reduces the amount of the metal vapor 12 introduced into the measuring chamber 15. Due to said effect in addition to the partial reduction of the metal vapor 12 with the nitrogen gas 28, $28_1$, $28_2$, the amount of metal vapor 12 reaching the measuring beam 20 is remarkably reduced.

According to the present invention, the deposition amount of a plating metal is directly controlled by measuring the amount of the metal vapor passing through the guide duct 13 as abovementioned, so that the deposition amount can be accurately controlled with a quick response time. Due to the fact that the atomic absorption method is capable of measurement in a broad range with high sensitivity, the amount of the metal vapor can be measured with high accuracy over a broad range from very small amounts to large amounts.

In addition, since each metal vapor passing through the guide duct 13 is separately measured, the deposition amount of each metal can be independently controlled. Furthermore, even in the case where the surface of the source metal 11 is contaminated with the formed oxides which reduces the surface area effective for evaporation and causes the fluctuation of evaporation, the deposition amount is accurately controlled without being influenced by the contamination.

Other features of the present invention will be apparent from the following Examples.

EXAMPLE

Example 1

Figure 10:
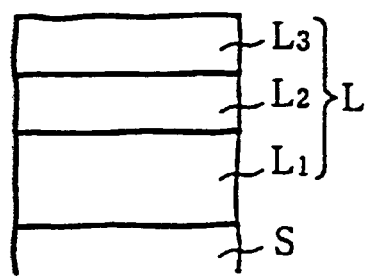
FIG. 10 is a schematic view illustrating a multi-layered structure of a Zn—Mg alloy plating layer obtained in Example 1.

A Zn—Mg vapor deposition coated steel sheet was manufactured by successively vapor depositing Zn, Mg and then Zn. The plating layer L formed in this way had a multi-layered structure, as shown in FIG. 10, comprising a Zn—Mg sublayer $L_1$ containing 0.5 wt. % or less Mg on a steel substrate S, a second Zn—Mg sublayer $L_2$ containing 2–20 wt. % and a third Zn—Mg sublayer $L_3$ containing 0.5 wt. % or less Mg. Since the properties of this vapor Zn—Mg deposition coated steel strip remarkably change in response to Mg content in the plating layer, it is especially important to control the amount of Mg deposited.

For the measurement of vapor amount by atomic absorption analysis, Zn or Mg vapor was sampled from the guide duct 13 and carried through the takeoff pipe 14 to the measuring chamber 15, wherein the Zn or Mg vapor was irradiated with the measuring beam 20 to detect absorbance.

In this Example, the guide duct 13 had a rectangular section of 500 mm in width, 100 mm in height and 3 m in length. The takeoff pipe 14 was of 2 mm in inner diameter and 1 m in length. An inlet pipe 27(shown in FIG. 15) of 0.5 mm in inner diameter and 10 mm in length was attached to the end of the takeoff pipe 14.

Figure 11:
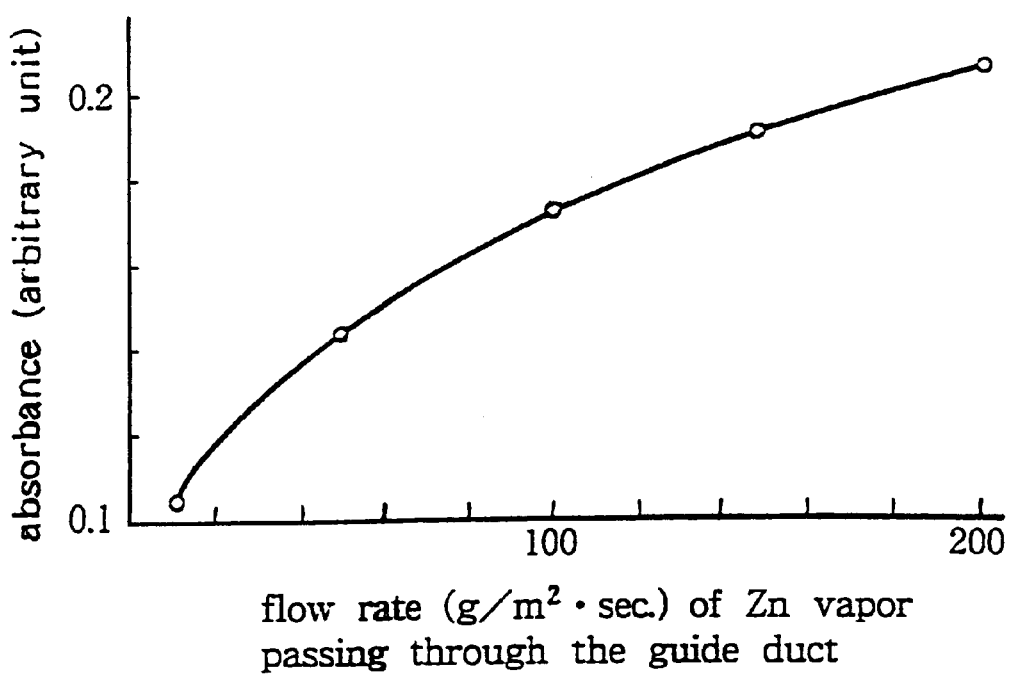
FIG. 11 is a graph showing the close relationship between the detected value of absorbance measured by atomic absorption analysis and the deposition amount of Zn measured by chemical analysis as represented by the flow rate of Zn vapor passing through the guide duct.
Figure 12:
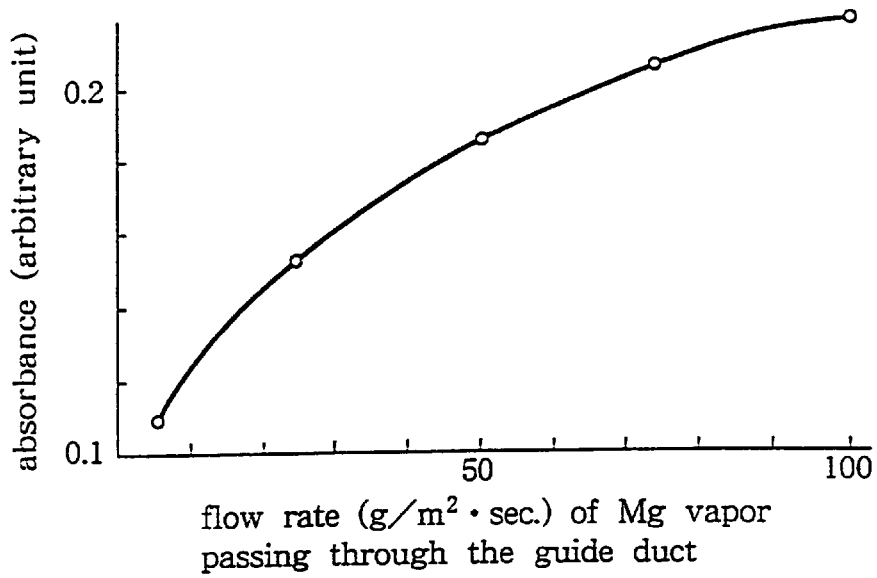
FIG. 12 is a graph showing the close relationship between the detected value of absorbance measured by atomic absorption analysis and the deposition amount of Mg measured by chemical analysis as represented by the flow rate of Mg vapor passing through the guide duct.

The measuring results of absorbance obtained by the atomic absorption analysis revealed a close relationship between the detected value of absorbance and the amounts of Zn and Mg vapors present, as shown in FIGS. 11 and 12, respectively. Using these close relationships, the amount of Zn or Mg vapor was calculated based on the detected value of absorbance for each metal.

The Zn—Mg plating layer was formed while controlling the deposition amount of each metal according to the atomic absorption method. The deposition amounts of Zn and Mg in the obtained plating layer were then measured by chemical analysis.

The values measured by the atomic absorption method were compared with those of the chemical analysis. It is noted from the comparison, as shown in Table 1, that there is high consistency between the values measured by the atomic absorption and those determined by chemical analysis. That is, the deposition amounts of the plating metals controlled by the atomic absorption method had the same reliability at a high level as those obtained by the chemical analysis. On the contrary, the fluorescent X-ray spectroscopy could not be adopted for the formation of the Zn—Mg plating layer having the necessary multi-layered structure, since it was impossible to measure the deposition amount of Mg.

TABLE 1

THE ACCURACY OF THE DEPOSITION AMOUNT ($g/m^2$) MEASURED BY ATOMIC ABSOROPTION SPECTROSCOPY

| Example No. | DEPOSITION AMOUNT OF PLATING LAYER | VALUE A | VALUE B | RATIO OF A/B |
|---|---|---|---|---|
| 1 | Zn | 19.7 | 19.4 | 1.02 |
|   | Mg | 0.65 | 0.68 | 0.96 |
| 2 | Zn | 19.4 | 19.1 | 1.02 |
|   | Mg | 0.88 | 0.84 | 1.05 |
| 3 | Zn | 18.9 | 19.8 | 0.95 |
|   | Mg | 1.19 | 1.21 | 0.98 |
| 4 | Zn | 29.0 | 29.6 | 0.98 |
|   | Mg | 0.92 | 0.90 | 1.02 |
| 5 | Zn | 28.7 | 27.5 | 1.04 |
|   | Mg | 1.33 | 1.30 | 1.02 |
| 6 | Zn | 28.1 | 26.1 | 1.08 |
|   | Mg | 1.84 | 1.87 | 0.98 |
| 7 | Zn | 49.5 | 50.2 | 0.98 |
|   | Mg | 1.35 | 1.31 | 1.03 |
| 8 | Zn | 68.5 | 69.2 | 0.98 |
|   | Mg | 1.98 | 2.01 | 0.98 |
| 9 | Zn | 66.2 | 65.7 | 1.01 |
|   | Mg | 4.00 | 4.11 | 0.97 |

Value A was obtained by atomic absorption spectroscopy.
Value B was obtained by chemical analysis.

Then, Zn and Mg were separately vapor deposited in a continuous line while changing target deposition amounts. The deposition amounts of Zn and Mg were individually measured by each of atomic absorption spectrum and by fluorescent X-ray spectroscopy, and the chronometric change of each deposition amount was calculated.

In this Example, a rectangular duct of 1 m in width, 300 mm in height and 3 m in length was used as the guide duct 13 for carrying Zn vapor, a cylindrical pipe of 2 mm in inner diameter and 1 m in length was used as the takeoff pipe 14, and an inlet pipe 27 (shown in FIG. 15) of 0.5 mm in inner diameter and 10 mm in length was attached to the end of the cylindrical pipe 14.

A rectangular duct of 1 m in width, 40 mm in height and 3 m in length was used as the guide duct 13 for carrying Mg vapor, and the same cylindrical pipe was used as the takeoff pipe 14 in this Example.

Figure 13:
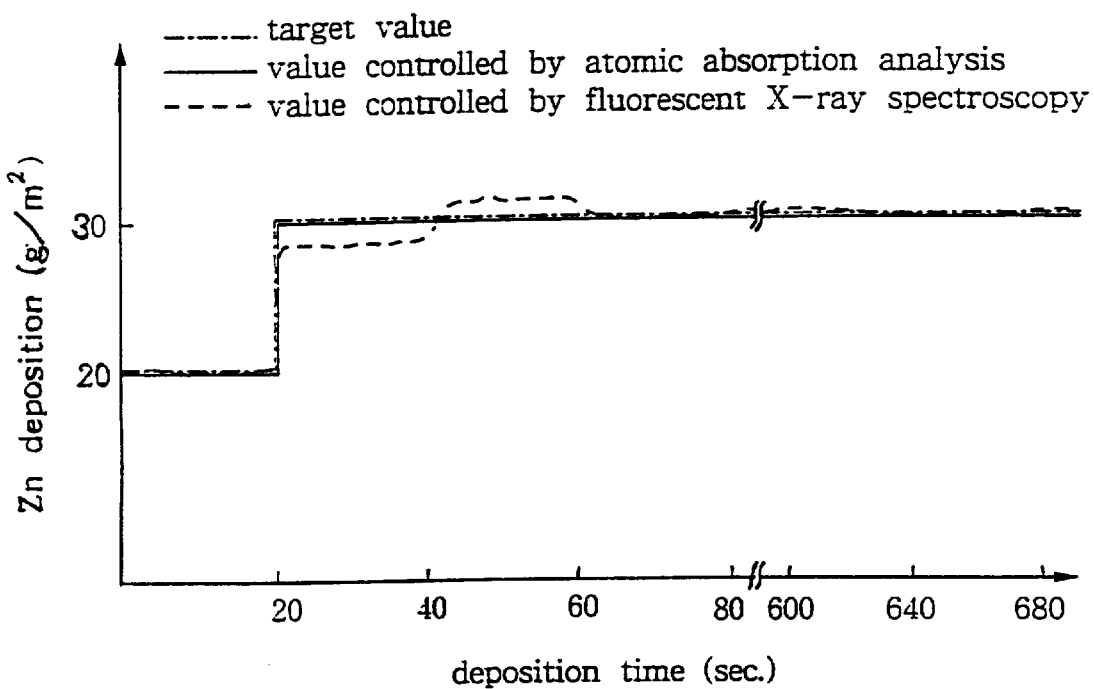
FIG. 13 is a graph showing the hunting of the deposition amount of Zn to a target value, when the deposition amount of Zn is measured and controlled by each of atomic absorption analysis and fluorescent X-ray spectroscopy.
Figure 14:
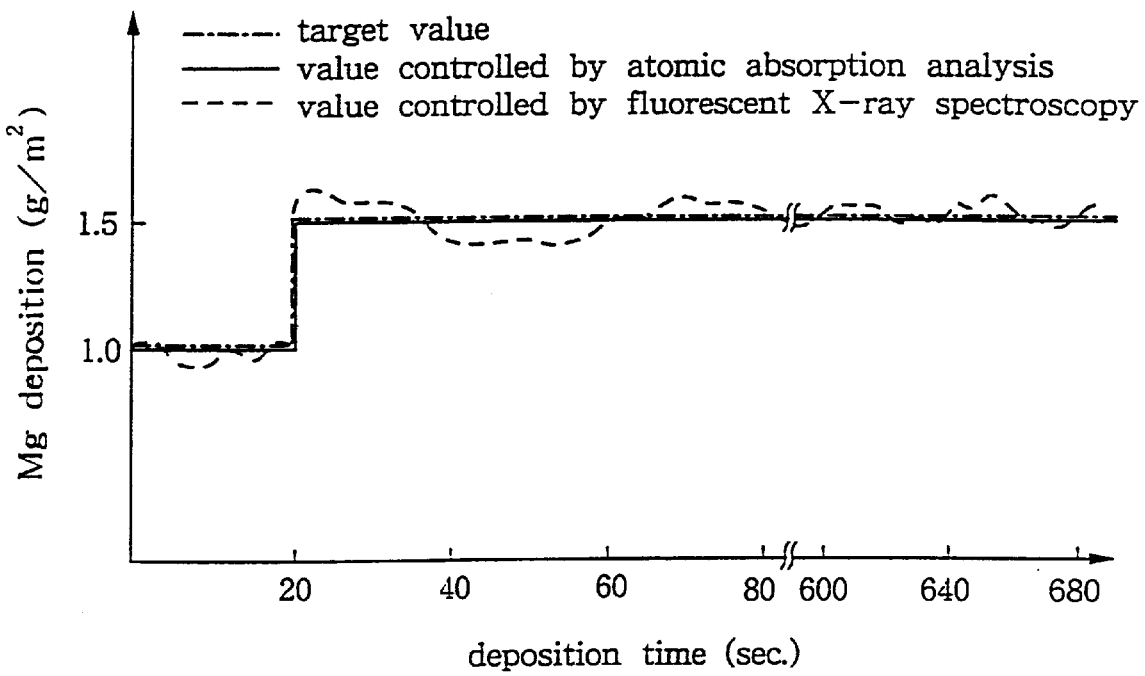
FIG. 14 is a graph showing the hunting of the deposition amount of Mg to a target value, when the deposition amount of Mg is measured and controlled by each of atomic absorption analysis and fluorescent X-ray spectroscopy.

In the case of the fluorescent X-ray spectroscopy which required a long time from vapor deposition to the measurement, the detected value of the amount of Zn deposition was hunted for a long period as shown in FIG. 13. Approximately 60 seconds were required until the deposition amount was stabilized at the target value. In addition, the accuracy of the measured amount of Mg deposition was quite poor, so that the deposition amount of Mg was unstable as shown in FIG. 14 even after the lapse of a long time.

On the other hand, the amounts of both Mg and Zn were measured with high accuracy by the atomic absorption photospectrum. Since the amount of each metal vapor was controlled in response to the detected value, the hunting period of the deposition amount was very short. Consequently, the deposition amounts of Zn and Mg were controlled to the target values in a few seconds, as also noted in FIGS. 13 and 14.

Example 2

Figure 15:
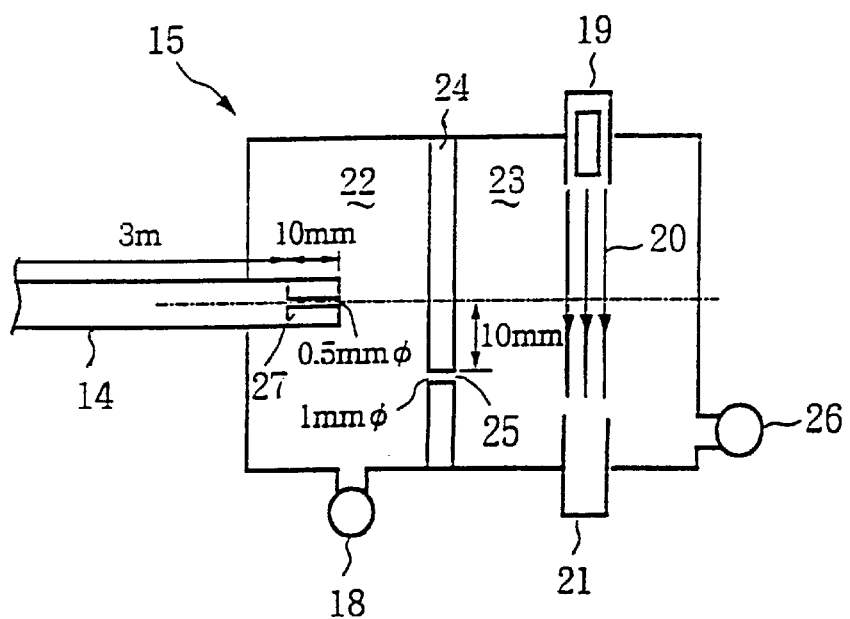
FIG. 15 is a schematic view showing the positional and dimensional relationship of various members in a measuring chamber used in Example 2.

The measuring chamber 15 in this Example was divided to a front compartment 22 and a rear compartment 23 by a partition wall 24, as shown in FIG. 15. The interior of a guide duct 13 was placed in communication with the interior of the measuring chamber 15 through the takeoff pipe 14 of 2 mm in inner diameter and 3 m in length to which an inlet pipe 27 of 0.5 mm in inner diameter and 10 mm in length was attached at its end. An opening 25 of 1 mm in aperture was formed in the partition wall 24 at a position offset by 10 mm from the longitudinal axis of the takeoff pipe 14 extending in a direction toward a detector 21.

A metal vapor 12 was carried from a vapor source 10 through the guide duct 13 to a steel strip 1, and the metal vapor 12 passing through the guide duct 13 was sampled through the takeoff pipe 14 into the measuring chamber 16.

Figure 16:
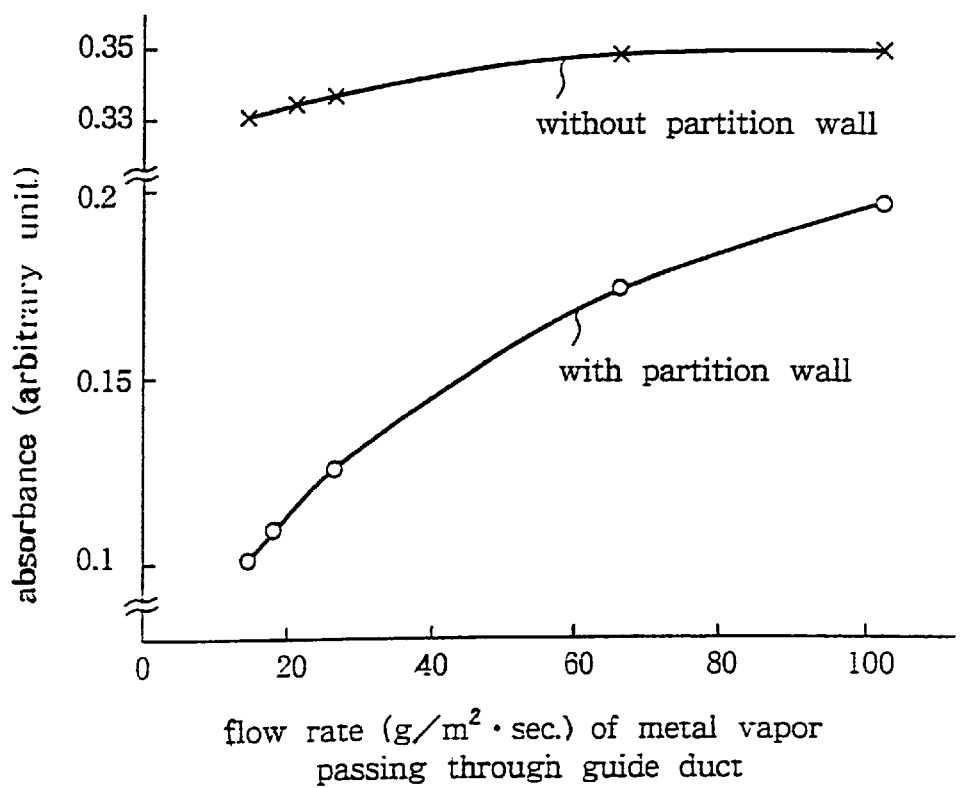
FIG. 16 is a graph showing the effect of a partition wall on the variation of absorbance.

The change of absorbance was studied in respect to the relationship with the change of the flow rate of the Mg vapor 12 passing through the guide duct 13. The result is shown in FIG. 16. It is noted that the absorbance variable within the range of 0.10–0.20 was measured.

In addition, the change of absorbance was examined under the same conditions, as above, except the partition wall 24 was removed. In this case, the absorbance varied within the narrower range of 0.33–0.35.

It is recognized from this comparison that the partition wall 24 made the variable range of the absorbance larger, resulting in a more accurate measurement of the flow rate of the Mg vapor 12 passing through the guide duct 13.

Figure 17:
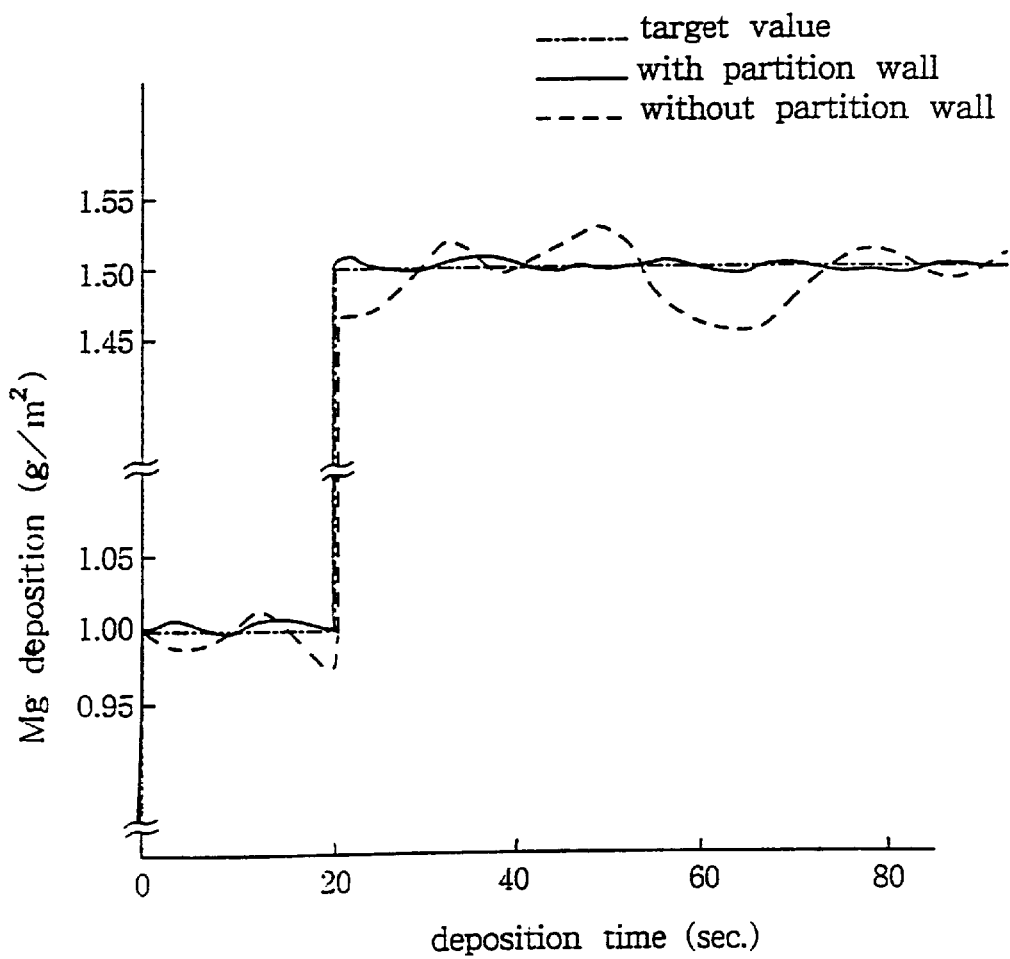
FIG. 17 is a graph showing the hunting of the deposition amount of Mg to a target value, when the deposition amount is controlled on the basis of a measured value obtained by using a measuring chamber divided by a partition wall.

The response time of the measurement was then examined by performing Mg vapor deposition in a continuous vapor deposition coating line while changing the target value of deposition. The result is shown in FIG. 17. It is noted that the deposition amount of Mg controlled by using the measuring chamber 15 equipped with the partition wall 24 provided the same responsiveness as the flow rate in the case without the partition wall 24. The consistency of the controlled deposition amount with the target value was remarkably improved, however, by the presence of the partition wall 24, as shown in FIG. 16, compared with the deposition amount controlled without the partition wall 24.

Example 3

The amount of metal vapor was reduced by purging it from the measuring chamber with nitrogen gas in this Example.

Figure 18:
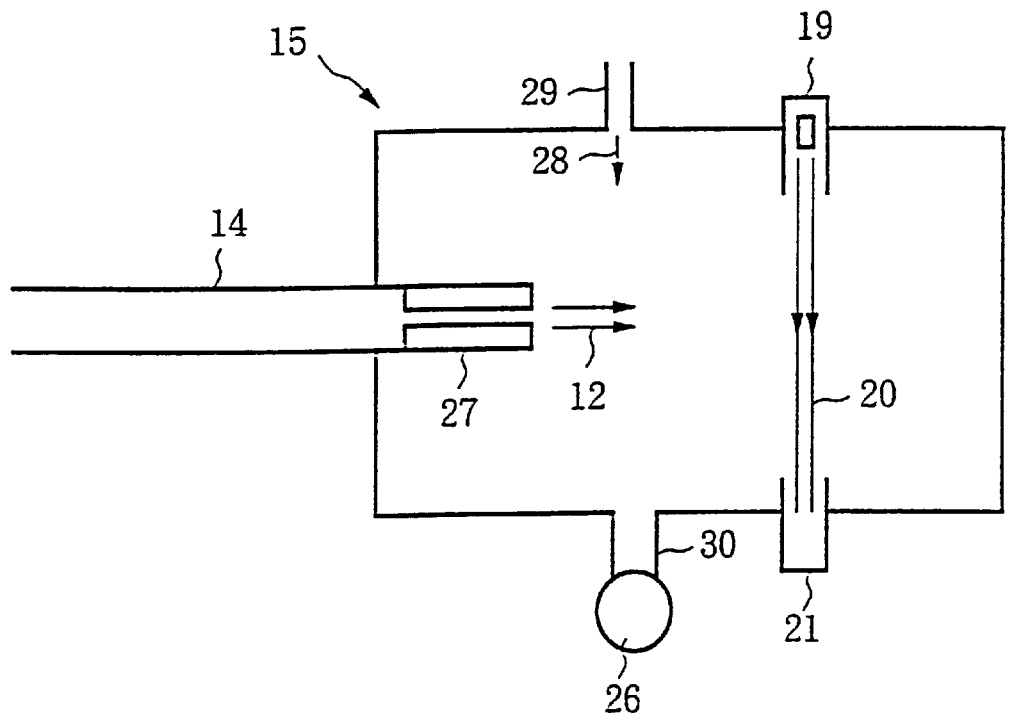
FIG. 18 is a schematic view illustrating a measuring chamber used in Example 3.

The guide duct 13 (shown in FIG. 2) was placed into communication with the measuring chamber 15 through the takeoff pipe 14 of 6 mm in inner diameter and 3 m in length. An inlet pipe 27 of 0.5 mm in inner diameter and 10 mm in length was attached to the end of the takeoff pipe 14, as shown in FIG. 18. A nitrogen gas supply pipe 29 was opened to the measuring chamber 15 at one side wall along a direction vertical to the flow axis of the metal vapor 12 introduced through the takeoff pipe 14 to the measuring chamber 15, and an exhaust pipe 30 was opened to the measuring chamber 15 at the opposite side wall.

The metal vapor 12 was carried from a vapor source 10 through the guide duct 13 to a steel strip 1 to be coated, as shown in FIG. 2. The metal vapor 12 passing through the guide duct 13 was sampled through the takeoff pipe 14 to the measuring chamber 15 at a flow rate of $1\times10^{-6}$ to $1\times10^{-3}$ g/m$^2$·sec. Nitrogen gas 28 was supplied through the nitrogen gas supply pipe 29 to the measuring chamber 15 at a constant flow rate of $1\times10^{-2}$ m$^2$·sec., and discharged together with most of the metal vapor 12 at a constant flow rate of $1\times10^{-2}$ g/m$^2$·sec. by a vacuum pump 18. In this case, the flow rate of the nitrogen gas supplied to the measuring chamber 15 and the flow rate of the gas discharged by the vacuum pump 18 depended on the degree of vacuum in the measuring chamber 15. As these flow rates increased, the amount of metal vapor 12 reaching the measuring beam 20 was reduced.

Figure 19:
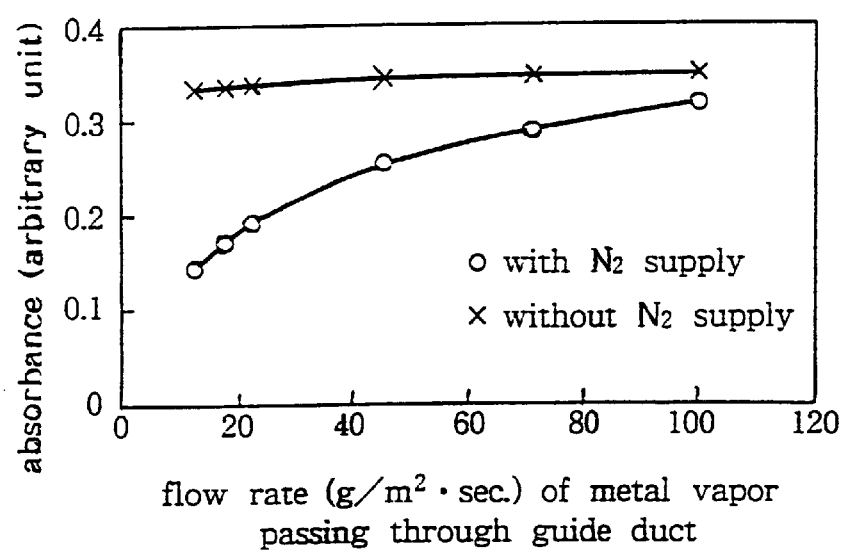
FIG. 19 is a graph showing the effect of nitrogen gas supply to purge metal vapor from the measuring chamber on the variation of absorbance.

The inventors examined the deviation of absorbance in relation to the flow rate of the metal vapor 12 passing through the guide duct 13. In this case, the absorbance varied within the range of 0.13 to 0.30, as shown in FIG. 19.

In addition, the deviation of absorbance was also examined under the same condition as above, but without the nitrogen gas supply. In the latter case, the deviation of absorbance was narrower and fell within the range of 0.34 to 0.35.

It is apparent from this comparison that the variation of absorbance was made larger by the supply and discharge of nitrogen gas. As a result, the flow rate of the metal vapor 12 passing through the guide duct 13 can be detected with higher accuracy when using the nitrogen flush.

Figure 20:
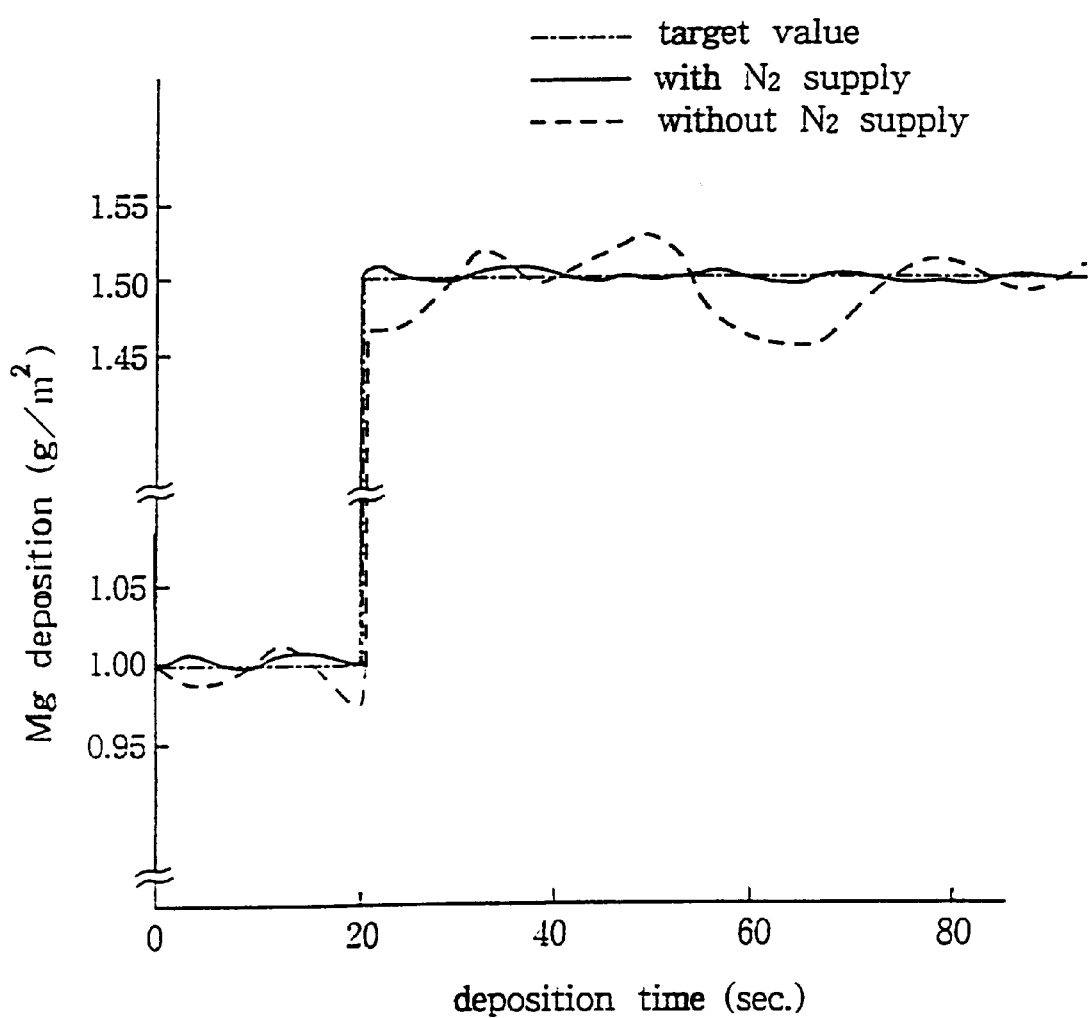
FIG. 20 is a graph showing the hunting of the deposition amount of Mg to a target value, when the deposition amount is controlled on the basis of a measured value obtained by supplying and discharging nitrogen gas to reduce the amount of Mg vapor.

The response time of measurement was then examined by performing Mg vapor deposition in a continuous vapor deposition coating line while changing the target value of deposition. The result is shown in FIG. 20. It is noted that the deposition amount of Mg was controlled with a quick response, even when most of the metal vapor 12 was discharged from the measuring chamber 15 by the supply and discharge of the nitrogen gas. The consistency of the controlled deposition amount with the target value was remarkably improved, compared with the deposition amount controlled without the supply and discharge of nitrogen gas.

According to the present invention as abovementioned, the flow amount of a metal vapor carried through a guide duct from a vapor source to a steel strip is directly measured by atomic absorption analysis. When the flow amount of the metal vapor is controlled on the basis of the measured value, the deposition amount of the metal can be controlled with a quick response time. In addition, the deposition amount of Mg can be accurately measured without the inclusion of measurement errors.

In the case where the absorbance is saturated but not increased any more due to the excessive inflow of the metal vapor, the amount of metal vapor reaching a measuring beam is reduced to a level sufficiently lower than the value at which the absorbance is saturated, by dividing the measuring chamber into a plurality of compartments or by purging most of the metal vapor with nitrogen gas. Due to the reduction in the amount of the metal vapor, the amount of the metal vapor passing through the guide duct is calculated from the detected value of absorbance with a high degree of accuracy.

The measured value represents the amount of the metal vapor carried through the guide duct with high responsiveness, since the amount of the metal vapor reaching the measuring beam instantaneously changes in response to the amount of the metal vapor passing through the guide duct, and since the takeoff pipe is opened to the guide duct at a position near the shutter for controlling the flow rate of the metal vapor passing through the guide duct.

Therefore, when the amount of the metal vapor carried to a steel strip is controlled on the basis of the measured value, the deposition amount of a plating metal can be adjusted to a target value with high consistency and within a quick response period. As a result, a vapor deposition coated steel strip manufactured in this way is extremely stabilized in quality.

What is claimed is:
1. A method of controlling the deposition amount of a plating metal in a continuous line for manufacturing a vapor deposition coated steel strip, comprising the steps of;

sampling a metal vapor from a guide duct which carries a metal vapor from a vapor source to a steel strip to be coated, carrying said sampled metal vapor through a takeoff pipe to a decompressed measuring chamber located outside of said guide duct, wherein a light source and a detector are provided, irradiating said sampled metal vapor with a measuring beam emitted from said light source, detecting said measuring beam after the irradiation by said detector so as to detect a value of absorbance of luminous energy in said sampled metal vapor, calculating a flow amount of said metal vapor passing through said guide duct from the detected value of absorbance, and controlling an opening ratio of a shutter provided in said guide duct on the basis of the calculation result so as to control the flow amount of the metal vapor passing through said guide duct.

2. The method according to claim 1, wherein the measuring beam is of a wavelength which is absorbed by the metal vapor.

* * * * *

UNITED STATES PATENT AND TRADEMARK OFFICE
CERTIFICATE OF CORRECTION

PATENT NO.   : 6,060,109
DATED        : May 9, 2000
INVENTOR(S)  : Hiroshi Tananka et al.

It is certified that error appears in the above-identified patent and that said Letters Patent is hereby corrected as shown below:

Title Page, ABSTRACT,
Line 17, "metal vapor 2" should read --metal vapor 12--.

Column 2,
Line 11 "structure" should read --structures--.

Column 8,
Line 64, "abovementioned" should read --above-mentioned"

Column 9,
Line 15, "example" should read --EXAMPLES--

Column 10,
Table 1 heading: "(g/m$^2$)" should read --(g/m$^2$)

Column 12,
Line 29, "abovementioned" should read --above-mentioned--

UNITED STATES PATENT AND TRADEMARK OFFICE
CERTIFICATE OF CORRECTION

PATENT NO. : 6,060,109
DATED : May 9, 2000
INVENTOR(S) : Hiroshi Tananka et al.

It is certified that error appears in the above-identified patent and that said Letters Patent is hereby corrected as shown below:

Claim 1, "of;"
Line 67, "of;" should read --of:--

Claim 1, Column 14,
Line 6, before "metal;" insert --sampled--.

Signed and Sealed this

Twenty-sixth Day of June, 2001

*Attest:*

NICHOLAS P. GODICI
*Attesting Officer*     *Acting Director of the United States Patent and Trademark Office*